(12) United States Patent
Zager

(10) Patent No.: US 7,060,307 B2
(45) Date of Patent: Jun. 13, 2006

(54) TOPICAL COMPOSITION FOR HEIGHTENED SENSITIVITY

(76) Inventor: Marilyn V. Zager, 122 S. 10th St., LaCrosse, WI (US) 54601

(*) Notice: Subject to any disclaimer, the term of this patent is extended or adjusted under 35 U.S.C. 154(b) by 54 days.

(21) Appl. No.: 10/723,697

(22) Filed: Nov. 26, 2003

(65) Prior Publication Data

US 2004/0109898 A1  Jun. 10, 2004

Related U.S. Application Data

(60) Provisional application No. 60/432,383, filed on Dec. 9, 2002.

(51) Int. Cl.
*A61K 35/78* (2006.01)
(52) U.S. Cl. ........................ 424/725; 514/627
(58) Field of Classification Search ................ 424/725; 514/627
See application file for complete search history.

(56) References Cited

U.S. PATENT DOCUMENTS

| | | | | |
|---|---|---|---|---|
| 4,780,309 A | * | 10/1988 | Geria et al. | 424/45 |
| 4,801,587 A | * | 1/1989 | Voss et al. | 514/248 |
| 5,770,206 A | * | 6/1998 | Nicolicchia | 424/739 |
| 5,869,533 A | * | 2/1999 | Holt | 514/627 |
| 6,428,791 B1 | * | 8/2002 | Lezdey et al. | 424/195.17 |

* cited by examiner

*Primary Examiner*—Patricia Leith
(74) *Attorney, Agent, or Firm*—Tipton L. Randall

(57) ABSTRACT

The invention is directed to a topical composition for heightened sensitivity and arousal for humans. The topical composition includes an organic fluid carrier, preferably glycerin, containing an effective amount of capsaicinoids extract, the active principle in chili peppers. In a further embodiment of the invention, the topical composition includes honey and evening primrose oil, in addition to capsaicinoids extract in the glycerin carrier. The present invention also includes a method for heightened sensitivity and arousal for humans. The method includes providing a topical composition, including an organic fluid carrier, preferably glycerin, containing an effective amount of capsaicinoids extract, and applying the topical composition to the genital area of a human to produce heightened sensitivity and arousal.

5 Claims, No Drawings

TOPICAL COMPOSITION FOR HEIGHTENED SENSITIVITY

CROSS-REFERENCE TO RELATED APPLICATIONS, IF ANY

This application claims the benefit under 35 U.S.C. § 119 (e) of co-pending provisional application Ser. No. 60/432,383, filed 9 Dec. 2002. Application Ser. No. 60/432,383 is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates to a topical composition for heightened sensitivity. More particularly, the present invention relates to a topical composition for heightened sensitivity and arousal. Most particularly, the present invention relates to an organic topical composition for sexual arousal and heightened sensitivity for humans.

2. Background Information

The active principle that causes the heat in chili peppers is a crystalline alkaloid generically called capsaicin. It is produced by glands at the junction of the placenta and the pod wall of the chili pepper. The capsaicin spreads unevenly throughout the inside of the pod and is concentrated mostly in the placental tissue. Capsaicin is an incredibly powerful and stable alkaloid seemingly unaffected by cold or heat, which retains its original potency despite time, cooking, or freezing. Although it has no odor or flavor, it is one of the most pungent compounds known, detectable to the palate in dilutions of one to seventeen million. It is slightly soluble in water, but very soluble in alcohols, fats, and oils.

Scientists have identified and isolated six naturally occurring capsaicinoids and one synthetic cousin, which is used as a reference gauge for determining the relative pungency of the others. The five major capsaicinoids contained in chili pepper extract are capsaicin (69%), dihydrocapsaicin (22%), and three minor related components: nordihydrocapsaicin (7%), homocapsaicin (1%), and homodihydrocapsaicin (1%). Capsaicin is 8-methyl-N-vanillyl-6-(E)-nonenamide and has the chemical composition $C_{18}H_{27}NO_3$. Dihydrocapsaicin is 8-methyl-N-vanillyl-nonanamide and has the chemical composition $C_{18}H_{29}NO_3$. Nordihydrocapsaicin is 7-methyl-N-vanillyl-octanamide and has the chemical composition $C_{17}H_{27}NO_3$. Homocapsaicin is 9-methyl-N-vanillyl-7-(E)-decenamide tand has chemical composition $C_{19}H_{29}NO_3$. Homodihydrocapsaicin is 9-methyl-N-vanillyl-decanamide and has the chemical composition $C_{19}H_{31}NO_3$. The synthetic capsaicinoid is the N-vanillylamide of n-nonanoic acid (VNA), having the systematic name N-vanillyl-nonanamide, with the chemical composition $C_{17}H_{27}NO_3$.

The pungency of the capsaicinoids is measured using the Scoville Organoleptic Test. The Scoville Test involves dilution of a given capsaicinoid with sugar water and tasting of the diluted capsaicinoid solution by a panel of individuals. The magnitude of dilution required to reach the taste threshold, where individuals cannot taste the pungent capsaicinoid equals the number of Scoville Units for that substance. For example, dilution of a material by 1:500,000 to reach the taste threshold indicates 500,000 Scoville Units for the material. The Scoville Unit (SU) rating for the pure, individual capsaicinoids are: Capsaicin—16 million SU; Dihydrocapsaicin—16 million SU; Nordihydrocapsaicin—9.1 million SU; Homocapsaicin—8.6 million SU, and Homodihydrocapsaicin—8.6 million SU. Extensive dilution of even a naturally occurring mixture of these capsaicinoids is required to allow for their use in ingested food materials.

There are dozens of brands of capsaicin creams on the market to combat the pain of arthritis, as well as shingles, psoriasis, and other skin disorders. One complaint about creams is that when applied, the creams bum the fingers and the user has a chance of getting some of the cream in his or her eyes. Therefor, Penecine Topical Pain Reliever is sold in three fluid ounce plastic containers that feature a hands-free roller ball applicator. Zostrix, one of the first creams on the market, is now available as Zostrix Topical Analgesic in stick form. It is advertised as portable, convenient, and drip-free. A single stick comes in a 0.7-ounce rack-displayable blister pack. Another application format is the patch. Capsaicin patches, like mustard plasters, have been available for years, but now they are making a comeback as Thera-Patch Penetrating Pain Relief Patches.

Other medical developments include the introduction of capsaicin gels and the addition of other medicines or herbs to make the capsaicin products more efficacious. Heritage Consumer Products has released Eucalyptamint 2000 arthritis pain relieving gel that contains capsaicin and menthol. Another analgesic gel is Arthogesic, which claims to give temporary relief from minor muscle aches, joint arthritis, backache, bruises, strains, and sprains.

Some manufacturers believe that the addition of herbal remedies assists the capsaicin. Sports Med and Arth DR utilize capsaicin plus glucosamine, raspberry leaf, valerian, and white willow bar. Capsaicin Gel, manufactured by Nature's Sunshine Product's, has twice as much capsaicin as most products (0.05 rather than 0.025 percent), plus yucca, horsetail, camomile, elder flower, peppermint oil, spearmint oil, aloe vera, and allantoin, a component of comfrey herb. Nature Works manufactures Swedish Bitters Capsaicin Cream, which contains capsaicin and Swedish Bitters extract for use in treating arthritis, backache, and pains in the muscles and joints.

One company, Thione International, has been granted a U.S. patent for its compositions for relief of the symptoms of arthritis. The patent protects Thione's healthcare preparations that are based on L-glutathione, "the body's key protector and most important antioxidant," according to company spokesmen Dr. Theodore Hersh. The first Thione product based upon the patent is Pain Relief Rx, which combines the company's antioxidant complex with capsaicin.

In general, the amount of capsaicin in these products, 0.01% to 0.05%, may be suitable for application to the skin of an individual for pain relief to the underlying muscles, but care must be taken to prevent contact of the mixture with the genital area which displays greater sensitivity to these materials.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention, as defined by the appended claims.

SUMMARY OF THE INVENTION

The invention is directed to a topical composition for heightened sensitivity and arousal for humans. The topical composition includes an organic fluid carrier, preferably glycerin, containing an effective amount of capsaicinoids, the active principle in chili peppers. In a further embodiment of the invention, the topical composition includes honey, and evening primrose oil, in addition to capsaicinoids in the organic fluid carrier. The present invention also includes a method for heightened sensitivity and arousal for humans. The method includes providing a topical composition including an organic fluid carrier, preferably glycerin, carrier containing an effective amount of capsaicinoids, and applying the topical composition to the genital area of a human to produce heightened sensitivity and arousal.

DESCRIPTION OF THE EMBODIMENTS

The invention is directed to a topical composition for heightened sensitivity and arousal for humans. The topical composition includes an organic fluid carrier, preferably glycerin, containing an effective amount of capsaicinoids, the active principle in chili peppers. The active principle is preferably a naturally occurring mixture of capsaicinoids, containing approximately 69% capsaicin, 22% dihydrocapsaicin, 7% nordihydrocapsaicin, 1% homocapsaicin, and 1% homodihydrocapsaicin, although a purified form of any one of these capsaicinoids may be used, as well. The naturally occurring mixture of capsaicinoids derived from chili peppers in a concentrated form is termed capsaicinoids extract. Capsaicinoids extract is available as a 3% solution in an organic fluid carrier, such as glycerin or soybean oil, from Garden Row Foods, 411 Stone Drive, St. Charles, Ill. 60174, as well as other commercial sources. The 3% solution is rated at 500,000 Scoville Units. The organic fluid carrier includes oils, such as soybean oil, peanut oil, corn oil, cotton seed oil, olive oil, canola oil, almond oil, propylene glycol, and mixtures thereof, as well as semi-solids, such as lanolin, lanolin alcohol, coco butter and mixtures thereof. Preferably the organic carrier is glycerin. Glycerin is 1,2,3-propanetriol, $C_3H_8O_3$, and is a well-known bulk chemical available from numerous commercial sources. Preferably, the glycerin is derived from a plant source and, most preferably, from an organically grown plant source. Organic vegetable glycerin is available from Starwest Botanicals, 11253 Trade Center Drive, Ranch Cordova, Calif. 95742.

An example preparation of the topical composition of the present invention is provided using glycerin as the fluid organic carrier, although the other organic fluids listed above may be used with equivalent results. The proportions used to prepare the topical composition of the present invention are one quart (946.35 mL) of glycerin carrier with five (5) to eight (8) drops of a 3% capsaicinoids extract in an organic fluid carrier, described above, added thereto. One milliliter (mL) contains 25 drops, thus 5 drops equal 0.2 mL, of which 3% (0.006 mL) is capsaicinoids extract. Likewise, 8 drops equal 0.32 mL, of which 3% (0.0096 mL) is capsaicinoids extract. The proportion of capsaicinoids extract:glycerin, by volume, in the topical composition is in the range of 1:157,725 to 1:98,578. Based upon a value of 500,000 Scoville Units for the 3% solution of capsaicinoids extract, the glycerin/capsaicinoids extract solutions prepared in the above proportions is expected to exhibit a Scoville Unit range of about 106 SU to 169 SU.

Alternatively, a purified individual capsaicinoid can be used to prepare the topical composition of the present invention with equivalent results. The mixture of capsaicinoids contained in chili pepper extract contains approximately 69% capsaicin, 22% dihydrocapsaicin, 7% nordihydrocapsaicin, 1% homocapsaicin, and 1% homodihydrocapsaicin, as described above. Because capsaicin plus dihydrocapsaicin, each rated at 16 million Scoville Units, comprise about 91% of the mixture, the dilution of a 3% solution of an individual capsaicinoid are essentially the same as for the dilution of the 3% capsaicinoids mixture extract, described above. Again, the proportions used to prepare the topical composition are one quart of glycerin carrier with five (5) to eight (8) drops of a 3% solution of an individual capsaicinoid added thereto. The proportion of individual capsaicinoid:glycerin, by volume, in the topical composition is in the range of 1:157,725 to 1:98,578.

In a further embodiment of the invention, the topical composition includes honey and evening primrose oil, in addition to the capsaicinoids extract in the glycerin carrier. Preferably, the honey used in the composition is raw organic honey, available from People's Food Co-op, La Crosse, Wis. 54601. The evening primrose oil is also available from People's Food Co-op, La Crosse, Wis. 54601. The proportions used to prepare the topical composition of the present invention are one quart of glycerin carrier, five (5) to eight (8) drops of 3% capsaicinoids extract in an organic fluid carrier added thereto, one (1) tablespoon (14.78 mL) of honey added thereto, and one-half (½) teaspoon (2.46 mL) of evening primrose oil added thereto. The ratio of capsaicinoids extract to honey is in the range of about 1:2,463 to about 1:1,540, and the ratio of capsaicinoids extract to evening primrose oil is in the range of about 1:410 to about 1:256.

Evening primrose oil is cold-pressed from the seeds of the evening primrose plant. The oil contains linolenic acid and the omega-6 fatty acid, gamma linolenic acid. Evening primrose oil is believed to fortify the production of gamma linolenic acid in the body to assure optimum levels of prostaglandins that are essential for proper organ function.

In yet a further embodiment of the invention, the topical composition further includes small amounts of food coloring to provide an appealing color thereto. Preferably, the topical composition of glycerin carrier containing an effective amount of capsaicinoids extract includes four (4) drops (0.16 mL) of red food coloring and three (3) drops (0.12 mL) of yellow food coloring added to one quart (946.35 mL) of the topical composition. Alternatively, one-half (½) teaspoon (2.96 mL) of molasses is added to one quart (946.35 mL) of the topical composition to impart a color thereto.

In yet a further embodiment of the invention, the topical composition further includes small amounts of vanilla extract to provide an appealing odor thereto. Preferably, the topical composition of glycerin carrier containing an effective amount of capsaicinoids extract includes twenty-five (25) drops (1.0 mL) of vanilla extract added to one quart (946.35 mL) of the topical composition.

The present invention also includes a method for heightened sensitivity and arousal for humans. The method includes providing a topical composition including an organic fluid carrier, preferably glycerin, containing an effective amount of capsaicinoids extract. The capsaicinoids extract/glycerin carrier topical composition is applied to the genital area of a human to produce heightened sensitivity and arousal. The general effects of the topical composition of the present invention include increased warmth and increased body fluid secretion, heightened sensitivity, vascular dilation in the application area and heightened sexual arousal. Both female and male humans experience these effects upon topical application of the composition of the present invention.

While the invention has been particularly shown and described with reference to preferred embodiments thereof, it will be understood by those skilled in the art that various changes in form and details may be made therein without departing from the spirit and scope of the invention.

I claim:

1. A topical composition for heightened sensitivity and arousal in humans comprising;
    (a) an organic fluid carrier present at about 98,578 parts to about 157,725 parts by volume;
    (b) capsaicinoids extract present at about 1 part by volume;
    (c) honey present at about 1540 parts to about 2463 parts by volume;
    (d) evening primrose oil present at about 256 parts to about 410 parts by volume;
    (e) a coloring material to impart a color to the topical composition; and
    (f) vanilla extract to impart an odor to the topical composition.

2. The topical composition for heightened sensitivity according to claim 1 wherein, the organic fluid carrier is selected from, the group consisting of glycerin, propylene glycol, soybean oil, peanut oil, corn oil. cotton, seed oil, olive oil, canola oil, almond oil, lanolin, lanolin alcohol, coco butter and mixtures thereof.

3. The topical composition for heightened sensitivity and arousal in humans of claim 1 wherein, the organic fluid cater is glycerin.

4. A topical composition for heightened sensitivity comprising;
    (a) about 98,578 parts to about 157,725 parts by volume of glycerin;
    (b) about one part by volume of capsaicinoids extract;
    (c) about 1540 parts to about 2463 parts by volume of honey;
    (d) about 256 parts to about 410 parts by volume of evening primrose oil;
    (e) a coloring material to impart a color to the topical composition; and
    (f) vanilla extract to impart an odor to the topical composition.

5. The topical composition for heightened sensitivity according to claim 4 wherein the glycerin is organic vegetable glycerin.

* * * * *